United States Patent
Axt et al.

(10) Patent No.: US 7,060,712 B2
(45) Date of Patent: Jun. 13, 2006

(54) CRYSTALLINE FORM OF ARYL ANILINE $\beta_2$ ADRENERGIC RECEPTOR AGONIST

(75) Inventors: Sabine Axt, Sunnyvale, CA (US); Ioanna Stergiades, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 10/841,761

(22) Filed: May 7, 2004

(65) Prior Publication Data

US 2004/0224982 A1    Nov. 11, 2004

Related U.S. Application Data

(60) Provisional application No. 60/468,810, filed on May 8, 2003.

(51) Int. Cl.
*A61K 31/47* (2006.01)
*C07D 215/20* (2006.01)

(52) U.S. Cl. ........................... 514/312; 546/157
(58) Field of Classification Search ................ 546/157; 514/312
See application file for complete search history.

(56) References Cited

U.S. PATENT DOCUMENTS

| | | | |
|---|---|---|---|
| 4,894,219 A | 1/1990 | Baker et al. | |
| 6,653,323 B1 * | 11/2003 | Moran et al. | 514/312 |
| 6,670,376 B1 * | 12/2003 | Moran et al. | 514/312 |
| 6,759,398 B1 | 7/2004 | Biggadike | |
| 2002/0019378 A1 | 2/2002 | Angell et al. | |
| 2003/0229058 A1 * | 12/2003 | Moran et al. | 514/171 |
| 2004/0059116 A1 | 3/2004 | Moran et al. | |
| 2004/0063755 A1 | 4/2004 | Moran et al. | |

FOREIGN PATENT DOCUMENTS

| | | |
|---|---|---|
| WO | WO 01/42193 A | 6/2001 |
| WO | WO 02/066422 A1 | 8/2002 |
| WO | WO 02/070490 A1 | 9/2002 |
| WO | WO 02/076933 A1 | 10/2002 |
| WO | WO 03/024439 A1 | 3/2003 |
| WO | WO 03/072539 A1 | 9/2003 |
| WO | WO 03/091204 A1 | 11/2003 |

OTHER PUBLICATIONS

"Functionalized Silica Gels for Organic Synthesis". ChemFiles vol. 2, No. 6, pp. 1-20; http://www.sigmaaldrich.com/img/assets/10640/Silica_Gel_BrochureNP.pdf, printed Aug. 6, 2004.

* cited by examiner

*Primary Examiner*—D. Margaret Seaman
(74) *Attorney, Agent, or Firm*—Jeffrey A. Hagenah; Roberta P. Saxon

(57) ABSTRACT

The invention provides crystalline solvate forms of a salt of a novel $\beta_2$ adrenergic receptor agonist. The invention also provides pharmaceutical compositions comprising the solvate forms, formulations containing the pharmaceutical compositions, methods of using the solvate forms to treat diseases associated with $\beta_2$ adrenergic receptor activity, and processes useful for preparing such solvate forms.

31 Claims, 4 Drawing Sheets

CRYSTALLINE FORM OF ARYL ANILINE β₂ ADRENERGIC RECEPTOR AGONIST

CROSS-REFERENCE TO RELATED APPLICATIONS

This application claims the benefit of U.S. Provisional Application No. 60/468,810, filed on May 8, 2003, the disclosure of which is incorporated herein by reference in its entirety.

FIELD OF THE INVENTION

The invention is directed to crystalline solvate forms of a salt of a $\beta_2$ adrenergic receptor agonist. The invention is also directed to pharmaceutical compositions comprising the solvate forms, formulations containing the pharmaceutical compositions, methods of using the solvate forms to treat diseases associated with $\beta_2$ adrenergic receptor activity, and processes useful for preparing such solvate forms.

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating pre-term labor, and are potentially useful for treating neurological disorders and cardiac disorders. Commonly assigned U.S. Pat. Nos. 6,653,323 B2 and 6,670,376 B1 disclose the novel compound N-{2-[4-(3-phenyl-4-methoxyphenyl)aminophenyl]ethyl}-(R)-2-hydroxy-2-(8-hydroxy-2(1H)-quinolinon-5-yl)ethylamine,

1

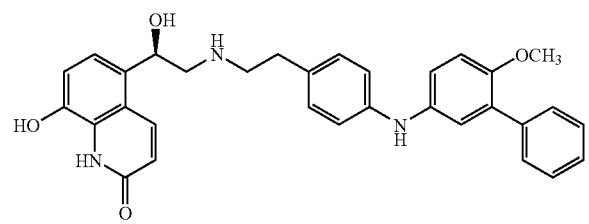

as a potent $\beta_2$ adrenergic receptor agonist. Compound 1 is alternatively referenced by the chemical name 8-hydroxy-5-((R)-1-hydroxy-2-{2-[4-(6-methoxybiphenyl-3-ylamino)-phenyl]ethylamino}ethyl)-1H-quinolin-2-one.

In order to purify and formulate medicinal compounds for use as therapeutic agents, it is advantageous to provide the compounds in crystalline form. No crystalline form of compound 1 or of a pharmaceutical salt thereof has been reported previously.

SUMMARY OF THE INVENTION

The present invention provides crystalline N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride in solvate form. In one aspect, the solvate form is a crystalline water and isopropanol solvate (hereinafter Form A). In a second aspect, the solvate form is a crystalline water hydrate (hereinafter Form B). Forms A and B of the monohydrochloride salt of compound 1 have been characterized by x-ray powder diffraction (XRPD), differential scanning calorimetry (DSC), infrared spectroscopy (IR), nuclear magnetic resonance spectroscopy (NMR), and by elemental analysis.

The invention also provides pharmaceutical compositions comprising Form A, Form B, or combinations thereof of the monohydrochloride salt of compound 1 and a pharmaceutically acceptable carrier. Further, the invention provides combinations comprising Form A, Form B, or combinations thereof of the monohydrochloride salt of compound 1 and one or more other therapeutic agents and pharmaceutical compositions comprising such combinations.

In another aspect, the invention provides a method of treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal, the method comprising administering to the mammal, a therapeutically effective amount of Form A, Form B, or combinations thereof of the monohydrochloride salt of compound 1. The invention also provides a method of treatment comprising administering a combination of a therapeutically effective amount of Form A, Form B, or combinations thereof of the monohydrochloride salt of compound 1 together with one or more other therapeutic agents.

The invention further provides the monohydrochloride salt of compound 1 in crystalline solvate form for use in medical therapy, as well as the use of the monohydrochloride salt of compound 1 in crystalline solvate form or of a pharmaceutical composition comprising the monohydrochloride salt of compound 1 in crystalline solvate form in the manufacture of a medicament for treating a disease or condition associated with $\beta_2$ adrenergic receptor activity in a mammal.

In a first synthetic method aspect, the invention provides a method of preparing Form A, the method comprising suspending a hydrochloride salt of compound 1 in a polar solvent comprising isopropanol and water, heating the suspension to between about 40° C. and about 60° C., and cooling the suspension to room temperature, resulting in the formation of Form A. In a second method aspect, the invention provides a method of preparing Form A from the free base of compound 1.

The invention further provides a method of preparing Form B, the method comprising forming a first water slurry of Form A material, isolating a solid material from the first water slurry, and forming a second water slurry from the isolated solid material, from which the hydrate Form B is obtained.

In yet another method aspect, this invention provides a method of reducing the amount of palladium in a composition comprising the diarylamine compound N-{2-[4-(3-phenyl-4-methoxyphenyl)aminophenyl]ethyl}-(R)-2-hydroxy-2-(8-benzyloxy-2(1H)-quinolinon-5-yl)ethylamine, an intermediate in the synthesis of compound 1, and palladium. The method comprises (a) contacting a solution comprising the diarylamine compound wherein each nitrogen atom has been protonated with an acid, palladium, and a solvent, with a functionalized solid support comprising (1-thioureido)alkyl or (mercapto)alkyl groups; and (b) separating the resulting solution from the solid support to provide a composition having a reduced amount of palladium, wherein the solvent is compatible with the functionalized solid support.

BRIEF DESCRIPTION OF THE DRAWINGS

The invention is illustrated by reference to the accompanying drawings.

DETAILED DESCRIPTION OF THE INVENTION

Figure 1:
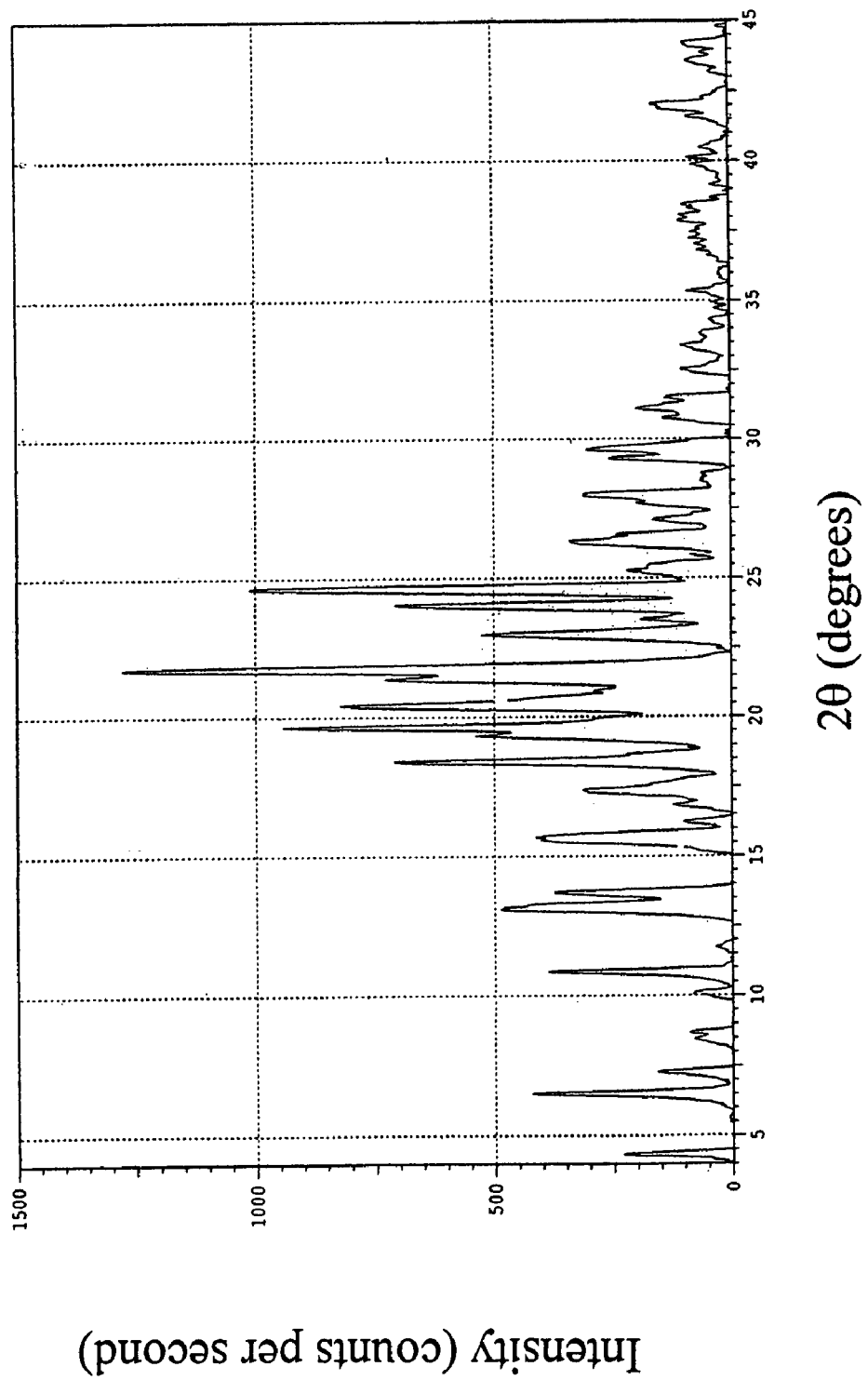
FIG. 1 shows an x-ray powder diffraction pattern of N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride water/isopropanol solvate (Form A).

When describing the compounds, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, bronchoconstrictive or pulmonary diseases, such as asthma and chronic obstructive pulmonary disease (including chronic bronchitis and emphysema), as well as neurological disorders and cardiac disorders. $\beta_2$ Adrenergic receptor activity is also known to be associated with pre-term labor (see U.S. Pat. No. 5,872,126) and some types of inflammation (see WO 99/30703 and U.S. Pat. No. 5,290,815).

The present invention provides crystalline N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride in solvate form. In a first aspect, the solvate is a crystalline water and isopropanol solvate (Form A). Form A is characterized by an x-ray powder diffraction (XRPD) pattern having two or more diffraction peaks at 2θ values selected from the group consisting of 13.12±0.2, 13.66±0.2, 15.56±0.2, 15.68±0.2, 17.39±0.2, 18.39±0.2, 19.32±0.2, 19.61±0.2, 20.42±0.2, 21.38±0.2, 21.72±0.2, 22.95±0.2, 23.50±0.2, 23.99±0.2, and 24.60±0.2. In particular, Form A of the present invention is characterized by an x-ray powder diffraction pattern having two or more diffraction peaks at 2θ values selected from the group consisting of 19.61±0.2, 20.42±0.2, 21.38±0.2, 21.72±0.2, and 24.60±0.2.

As is well known in the field of x-ray powder diffraction, relative peak heights of XRPD spectra are dependent on a number of factors having to do with sample preparation and instrument geometry, while peak positions are relatively insensitive to experimental details. Thus, the crystalline Form A of compound 1 is also characterized by an x-ray powder diffraction pattern in which the peak positions are substantially in accordance with those shown in FIG. 1.

Form A is further characterized by its infrared absorption spectrum which shows significant absorption bands at 626±1, 638±1, 643±1, 656±1, 698±1, 829±1, 1048±1, 1233±1, 1301±1, 1399±1, 1490±1, 1508±1, 1598±1, 1640±1, and in the range 3360–3480 cm$^{-1}$.

Figure 2:
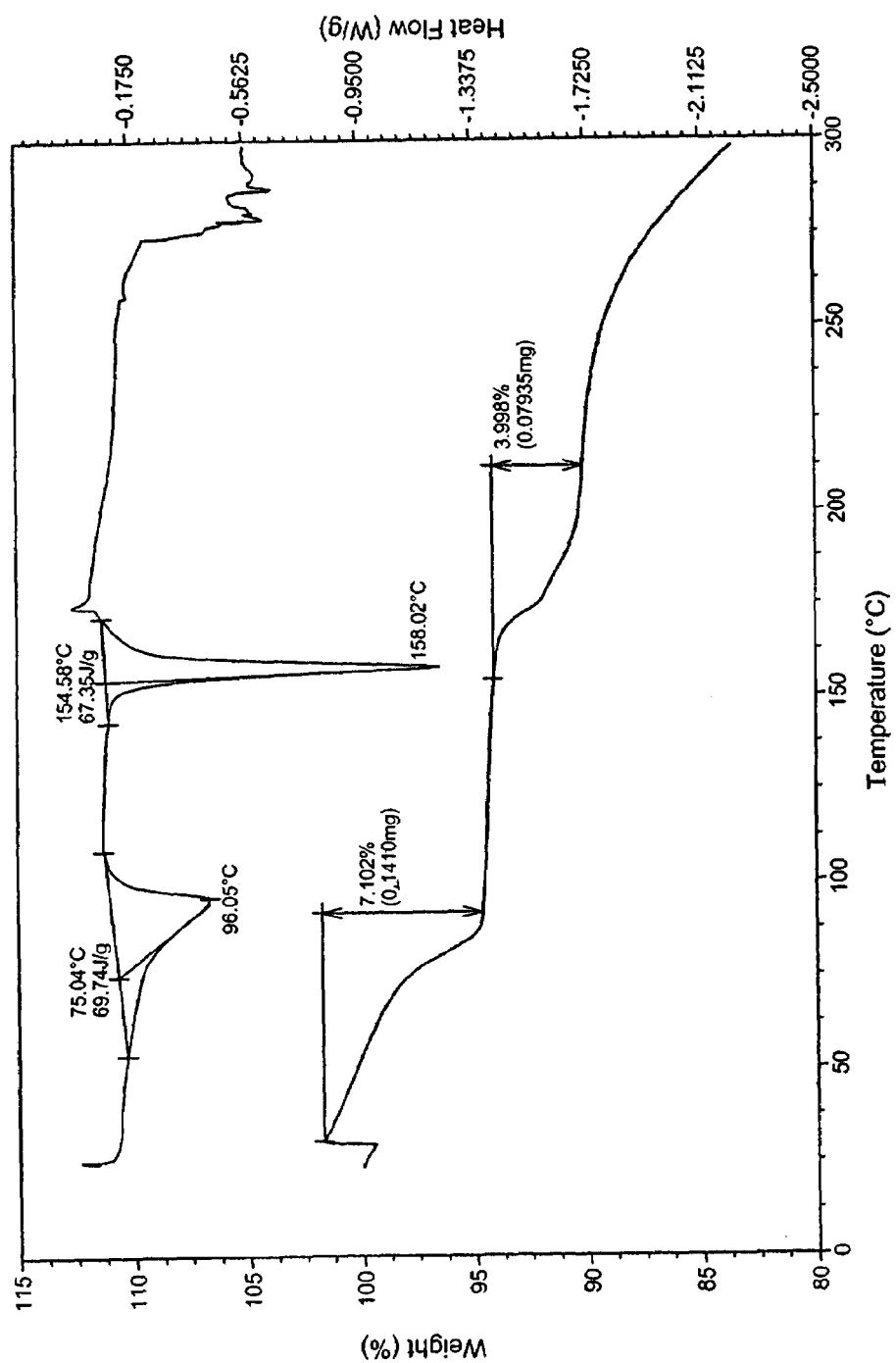
FIG. 2 shows a differential scanning calorimetry trace (top trace, right side scale) and thermogravimetric trace (bottom trace, left side scale) of N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride water/isopropanol solvate (Form A).

Form A of the present invention is yet further characterized by its differential scanning calorimetry trace which shows a broad endothermic feature between about 75 and 115° C. and a sharper endothermic feature between about 145 and about 165° C., as illustrated in FIG. 2. Without being bound to any theory of action, comparison of the DSC trace with thermogravimetric analysis data supports the inference that the lower temperature feature is associated with loss of isopropanol and water. The comparison also supports the interpretation that the higher temperature feature of the DSC trace may be associated with the onset of decomposition and/or loss of water or HCl, with significant decomposition initiating above 220° C.

Form A has been demonstrated to be stable upon storage for four weeks at 25° C. and 60% humidity in closed containers as evidenced by lack of increase in peaks associated with degradants in high pressure liquid chromatography (HPLC) results and by insignificant changes in DSC, TGA, and XRPD traces.

Solvate Form A contains between about 2 and about 4% (by weight) water and between about 2 and about 4% (by weight) isopropanol, which corresponds to between about 0.7 and 1.3 equivalents of water and between about 0.2 and about 0.4 equivalents of isopropanol per mole of compound 1 hydrochloride.

In a second aspect, the solvate form is a crystalline water hydrate (Form B). Form B is characterized by an x-ray powder diffraction (XRPD) pattern having two or more diffraction peaks at 2θ values selected from the group consisting of 13.26±0.2, 13.72±0.2, 15.66±0.2, 15.87±0.2, 17.43±0.2, 18.54±0.2, 19.44±0.2, 19.70±0.2, 20.54±0.2, 21.54±0.2, 21.82±0.2, 23.08±0.2, 24.12±0.2, and 24.69±0.2. In particular, Form B of the present invention is characterized by an x-ray powder diffraction pattern having two or more diffraction peaks at 2θ values selected from the group consisting of 20.54±0.2, 21.82±0.2, 23.08±0.2, 24.12±0.2, and 24.69±0.2.

Figure 3:
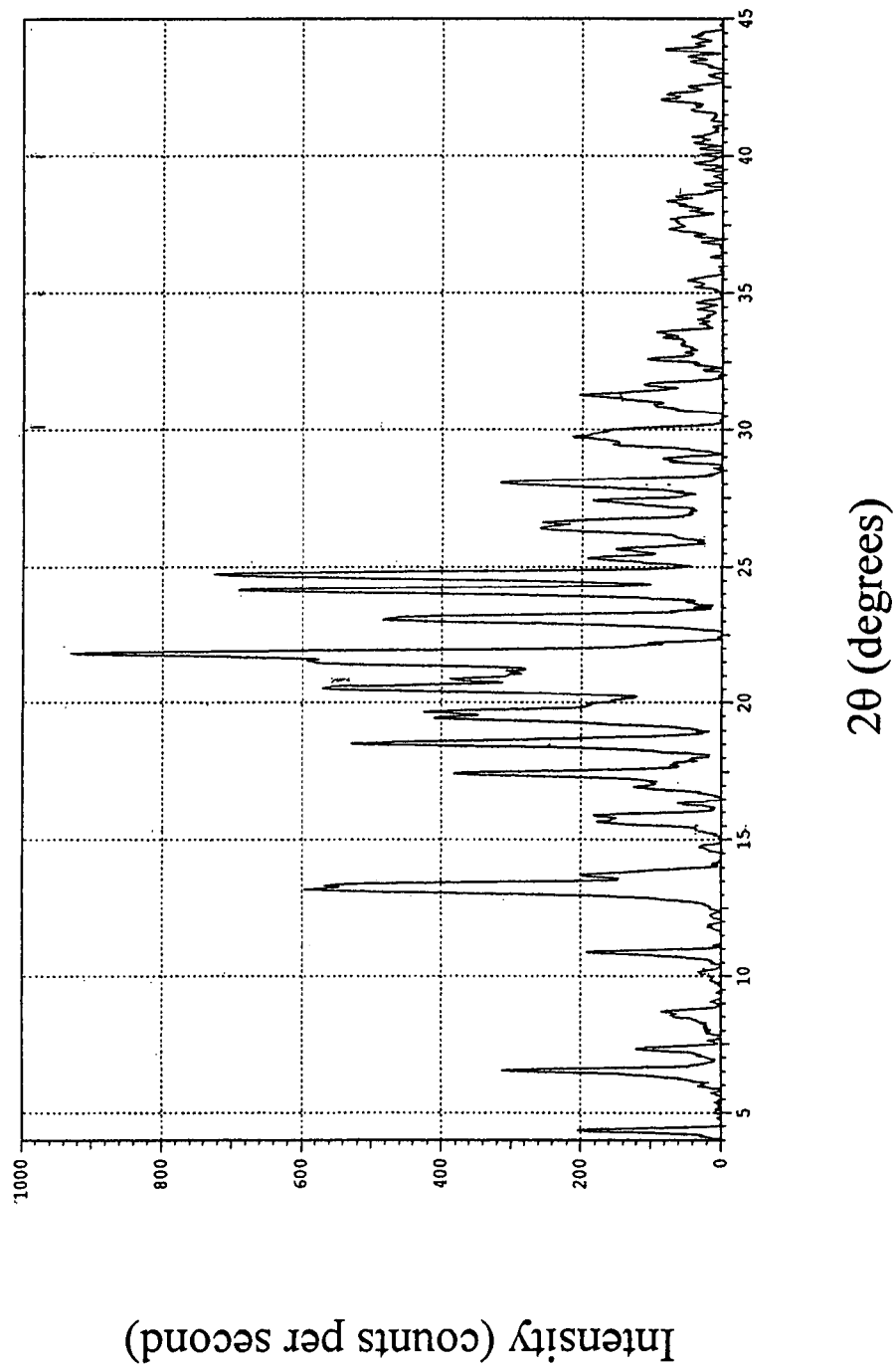
FIG. 3 shows an x-ray powder diffraction pattern of N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride hydrate (Form B).

Form B of compound 1 is also characterized by an x-ray powder diffraction pattern in which the peak positions are substantially in accordance with those shown in FIG. 3. Comparison of the x-ray powder diffraction patterns of Form A and Form B shows the peaks of Form B are shifted to higher 2θ values by an average of about 0.12 degrees.

Form B is further characterized by its infrared absorption spectrum which shows significant absorption bands at 653±1, 698±1, 829±1, 1232±1, 1262±1, 1383±1, 1445±1, 1488±1, 1508±1, 1548±1, 1598±1, 1640±1, 2831±1, 3033±1, and 3388±1 cm$^{-1}$.

Figure 4:
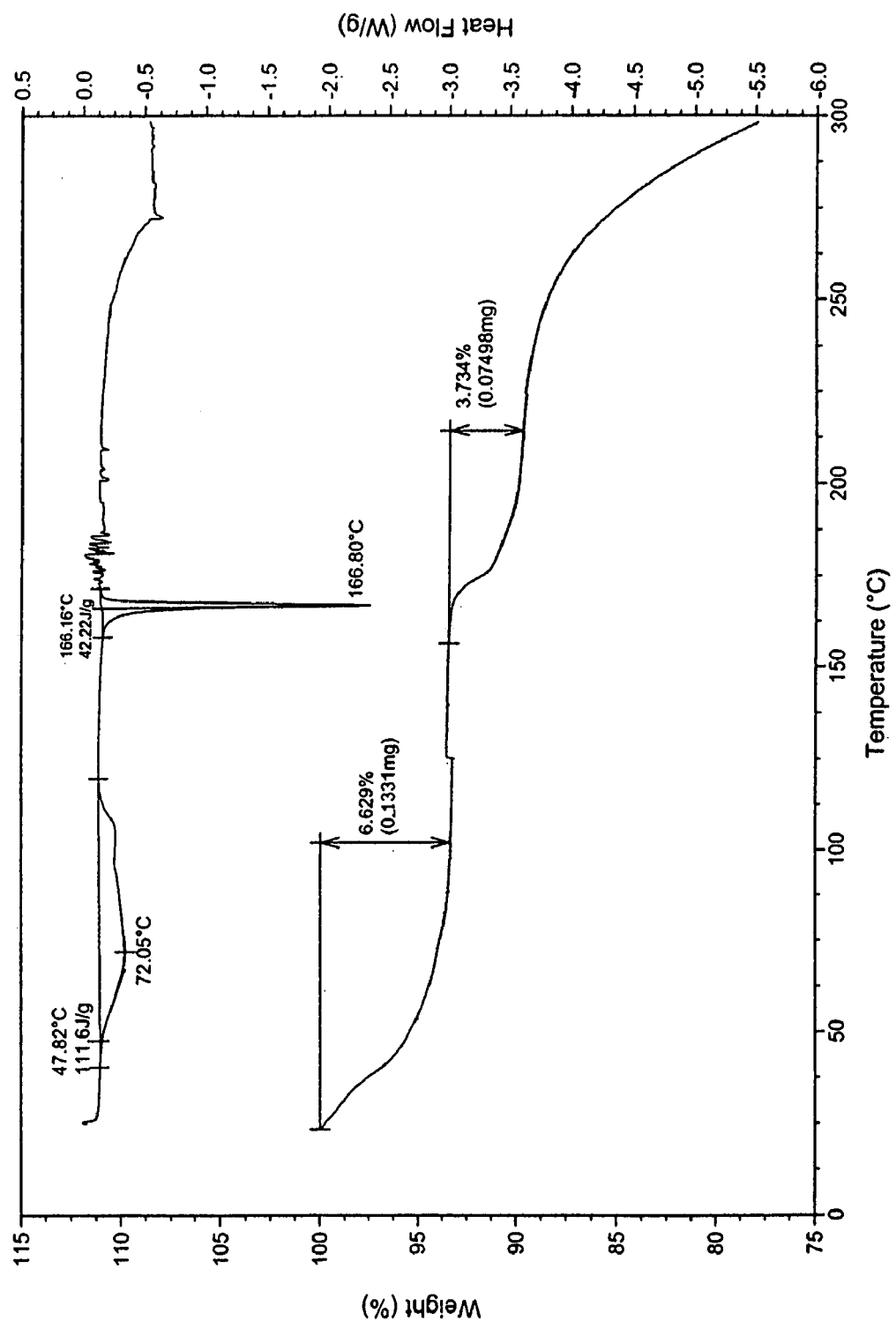
FIG. 4 shows a differential scanning calorimetry trace (top trace, right side scale) and thermogravimetric trace (bottom trace, left side scale) of N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride hydrate (Form B).

Form B of the present invention is yet further characterized by its differential scanning calorimetry trace exhibited in FIG. 4. The DSC trace of Form B shows a sharp endothermic feature at between about 150 and 170° C. Comparison of the DSC traces of Form A and Form B shows that the higher temperature endothermic feature of Form B is observed at a somewhat higher temperature than the comparable feature of Form A.

Form B contains between about 2% and about 7% water which corresponds to between about 0.7 and about 2.5 equivalents of water per mole of compound 1 hydrochloride.

The active agent, N-{2-[4-(3-phenyl-4-methoxyphenyl) aminophenyl]ethyl}-(R)-2-hydroxy-2-(8-hydroxy-2(1H)-quinolinon-5-yl)ethylamine (1), can be prepared from the benzyl protected intermediate N-{2-[4-(3-phenyl-4-methoxyphenyl)aminophenyl]ethyl}-(R)-2-hydroxy-2-(8-benzyloxy-2(1H)-quinolinon-5-yl)ethylamine (PP), which can be synthesized from readily available starting materials as shown in the following Scheme and further described in the Examples below. It will be appreciated that while specific process conditions (i.e. reaction temperatures, times, mole ratios of reactants, solvents, pressures, etc.) are given, other process conditions can also be used unless otherwise stated.

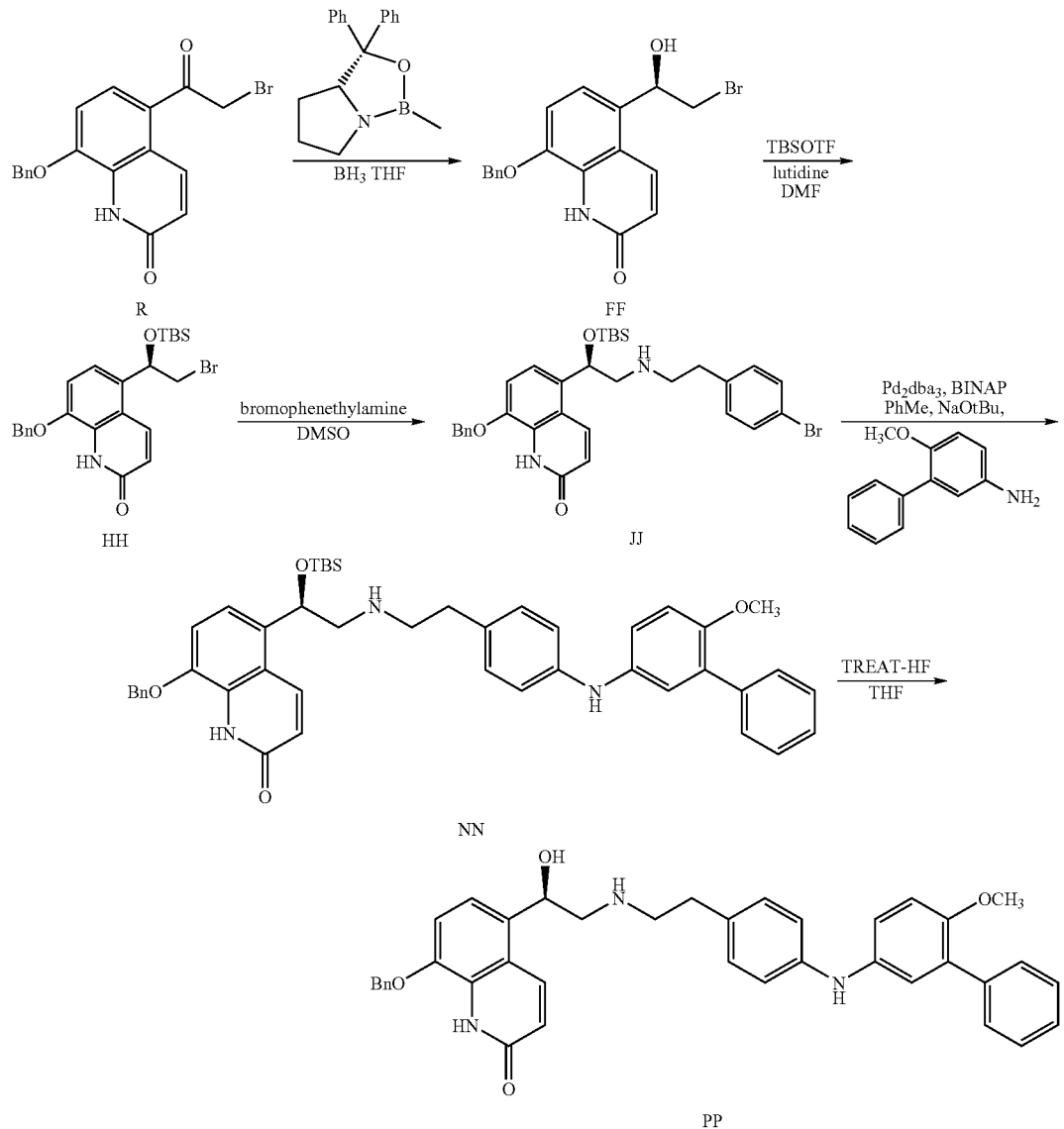

Scheme

Intermediate R, 5-(2-bromo-1-oxy)ethyl-8-benzyloxy-2(1H)-quinolinone, can be prepared as described in EP 147 791 B and analogously to the process described in WO 95/25104 for the corresponding chloroketone, as given in Example 1 below. Intermediate FF, 5-(2-bromo-(R)-1-hydroxy)ethyl-8-benzyloxy-2(1H)-quinolinone, can be formed by the chiral reduction of intermediate R using a oxazaborolidine catalyst prepared in situ following a procedure described in Mathre et al. *J. Org. Chem.*, 1991, 56, 751–762. The protected intermediate HH, 5-(2-bromo-(R)-1-tert-butyldimethylsiloxy)ethyl-8-benzyloxy-2(1H)-quinolinone, can be formed by the addition of tert-, butydimethylsilylchloride trifluoromethane sulfonate (TBSOTF) and lutidine to intermediate FF, dissolved in dimethylformamide (DMF).

Intermediate JJ, N-[2-(4-bromophenyl)ethyl]-(R)-2-tert-butyldimethylsiloxy-2-(8-benzyloxy-2(1H)-quinolinon-5-yl)ethylamine, is obtained as the solid hydrochloride salt by reaction of HH with 4-bromophenethylamine. Intermediate JJ is coupled, with 4-methoxy 3-phenylaniline hydrochloride in the presence of a catalyst comprising 2,2'-bis(diphenylphosphino)-1,1'-binaphthyl and tris(dibenzylideneacetone)dipalladium(0) to give the protected diarylamine intermediate NN, N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine. The TBS protecting group is removed from NN, dissolved in tetrahydrofuran (THF), by addition of triethylamine trihydrofluoride (TREAT HF), giving intermediate PP, N-{2-[4-(3-phenyl-4-methoxyphenyl)aminophenyl]ethyl}-(R)-2-hydroxy-2-(8-benzyloxy-2(1H)-quinolinon-5-yl)ethylamine.

The benzyl protecting group is removed from intermediate PP by catalytic hydrogenolysis, using palladium on activated carbon, with addition of concentrated hydrochloric acid to provide an amorphous hydrochloride salt of active compound 1, which can be further purified with decolorizing charcoal.

As described above, a palladium based catalyst was used in the coupling reaction to produce intermediate PP. As a result, the product, compound 1, or intermediates thereto, can be contaminated with unacceptable levels of palladium impurities. It has now been discovered that such palladium impurities can be removed from such intermediates, in particular, intermediate PP, using a functionalized solid support comprising (1-thioureido)alkyl or (mercapto)alkyl groups.

Intermediate PP is dissolved in a solvent compatible with the solid support, where a compatible solvent is one that does not affect the performance of the functionalized solid support. An amount of acid, preferably hydrochloric acid, sufficient to convert the basic nitrogens of the intermediate to protonated form is added. Between about 1.05 and about 1.2 equivalents of HCl per basic nitrogen is a sufficient amount. The resulting solution is diluted further with solvent and a functionalized solid support comprising (1-thioureido)alkyl or 3-(mercapto)alkyl groups is added. Preferably the solid support is a silica gel comprising 3-(1-thioureido)propyl or (mercapto)propyl groups. Preferably between about 5 and about 15% (by weight) of the functionalized silica gel is added. A preferred solvent compatible with the functionalized silica gel is a mixture of dichloromethane and methanol.

The resulting solution is separated from the solid support and the product is isolated. For example, the solution is stirred at room temperature for several hours followed by filtration through filter paper. The remaining silica is washed with additional solvent. Combined filtrates are washed with saturated aqueous sodium bicarbonate and brine. The organic solution is treated with anhydrous sodium sulfate, filtered, and evaporated under reduced pressure to give the product.

Accordingly, in a method aspect, this invention provides a method of reducing the amount of palladium in a composition comprising the diarylamine compound N-{2-[4-(3-phenyl-4-methoxyphenyl)aminophenyl]ethyl}-(R)-2-hydroxy-2-(8-benzyloxy-2(1H)-quinolinon-5-yl)ethylamine and palladium, the method comprising (a) contacting a solution comprising the diarylamine compound wherein each nitrogen atom has been protonated with an acid, palladium, and a solvent, with a functionalized solid support comprising (1-thioureido)alkyl or (mercapto)alkyl groups; and (b) separating the resulting solution from the solid support to provide a composition having a reduced amount of palladium, wherein the solvent is compatible with the functionalized solid support. Preferably, in the above method, the acid is hydrochloric acid; the solvent comprises a mixture of dichloromethane and methanol, and the functionalized solid support is a silica gel comprising 3-(1-thioureido)propyl or 3-(mercapto)propyl groups.

The crystalline water and isopropanol solvate (Form A) of the present invention can be formed by suspending the amorphous hydrochloride salt of compound 1 in a polar solvent comprising isopropanol and water, heating the suspension with stirring at a temperature of between about 40° C. and about 60° C., and allowing the suspension to cool to room temperature, resulting in the crystalline product. Preferably, the polar solvent is between about 40% and about 60% isopropanol.

For example, Form A can be formed by suspending the amorphous hydrochloride salt of compound 1 in a 50% water/isopropanol mixture, heating at a temperature of about 50° C. with stirring for over an hour and allowing the suspension to cool to room temperature at least overnight. The crystalline product can be isolated by filtration and dried under vacuum.

Alternatively, the crystalline water and isopropanol solvate (Form A) can be formed from the free base by suspending compound 1 in an aqueous polar solvent comprising isopropanol and water and a molar excess of of hydrochloric acid. Preferably the solvent contains between about 1.5 and about 2.5 equivalents of HCl. A preferred solvent is about 50% isopropanol/aqueous medium. The suspension is heated with stirring at a temperature of between about 40° C. and about 60° C., and allowed to cool to room temperature, resulting in the crystalline product, which can be isolated by filtration and dried under vacuum. The product can be recrystallized by suspending in a polar solvent, preferably isopropanol and water, heating with stirring at a temperature of between about 45° C. and about 55° C. and allowing to cool to room temperature, resulting in solvate Form A, which can be isolated and dried as above.

The crystalline water hydrate Form B can be prepared from solvate Form A by forming a water slurry of Form A material, stirring for an extended period, for example, about a day, filtering, and resuspending the filtered material in water and stirring for an additional extended period. The slurry is filtered and dried under vacuum to produce the hydrate Form B. As reported in Examples 8 and 12, analysis of residual solvent indicated a sample of Form B contained 0.2% isopropanol by weight, as compared with a sample of Form A, which contained 3.4% isopropanol.

Pharmaceutical Compositions

The solvates of the present invention, Form A and Form B, are advantageously used to prepare pharmaceutical compositions formulated for administration by inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 μm. Suitable nebulizer devices are provided commercially, for example, by PARI GmbH (Starnberg, Germany). Other nebulizer devices have been disclosed, for example, in U.S. Pat. No. 6,123,068. The present solvates can be formulated for use in a conventional nebulizer device as an aqueous solution at a concentration of between about 0.05 μg/mL and about 1 mg/mL of the free base active agent, compound 1.

DPI's typically administer a therapeutic agent in the form of a free flowing powder that can be dispersed in a patient's air-stream during inspiration. Alternative DPI devices which use an external energy source are also being developed. In order to achieve a free flowing powder, the therapeutic agent can be formulated with a suitable excipient (e.g., lactose). A dry powder formulation can be made, for example, by combining dry lactose having a particle size between about 1 μm and 100 μm with micronized particles of Form A, Form B, or a combination thereof and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3-heptafluoro-n-propane, (HFA 227) have been developed. Additional components of HFA formulations for MDI administration include co-solvents, such as ethanol, pentane, or minor amounts of water; and surfactants, such as sorbitan trioleate, oleic acid, lecithin, and glycerin. (See, for example, U.S. Pat. No. 5,225,183, EP 0717987 A2, and WO 92/22286).

Thus, a suitable formulation for MDI administration can include from about 0.001% to about 2% by weight of Form A, Form B, or a combination thereof, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the present crystalline form, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of the present crystalline material. (See, for example, WO 99/53901 and WO 00/61108). For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

The present active agent, compound 1, is useful as a $\beta_2$ adrenergic receptor agonist and therefore is useful for treating medical diseases or conditions mediated by $\beta_2$ adrenergic receptors or associated with $\beta_2$ adrenergic receptor activity in a mammal, i.e. medical conditions which are ameliorated by treatment with a $\beta_2$ adrenergic receptor agonist. Such medical conditions include but are not limited to a pulmonary disease, such as asthma or chronic obstructive pulmonary disease, pre-term labor, a neurological disorder, a cardiac disorder, or inflammation.

The present active agent, compound 1, is effective over a wide dosage range and is generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agent for inhalation administration are in the general range of from about 0.05 μg/day to about 1000 μg/day, preferably from about 0.1 μg/day to about 500 μg/day.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 μg/day to about 100 mg/day, preferably from about 0.5 μg/day to about 1000 μg/day.

The invention thus provides a method of treating a mammal having a disease or condition associated with $\beta_2$ adrenergic receptor activity, the method comprising administering to the mammal a therapeutically effective amount of the monohydrochloride salt of compound 1 in crystalline solvate form or of a pharmaceutical composition comprising the monohydrochloride salt of compound 1 in crystalline solvate form.

The present active agent can also be co-administered with one or more other therapeutic agents. For example, the present agent can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising Form A, Form B, or a combination thereof together with one or more therapeutic agent, for example, an anti-inflammatory agent, an antichlolinergic agent, another $\beta_2$ adrenergic receptor agonist, an antiinfective agent or an antihistamine.

The other therapeutic agents can be used in the form of pharmaceutically acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other β$_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol].

Other compounds of interest include:

Compounds set out in U.S. Pat. No. 5,552,438 issued Sep. 3, 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (Sept 6–10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19–23, Geneva) 1998]

1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methyl-benzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al J Pharmacol Exp Ther,1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine-CAS-51-55-8 or CAS-51-48-1 (anhydrous form), atropine sulfate -CAS-5908-99-6; atropine oxide-CAS-4438-22-6 or its HCl salt-CAS-4574-60-1 and methylatropine nitrate-CAS-52-88-0.

Homatropine-CAS-87-00-3, hydrobromide salt-CAS-51-56-9, methylbromide salt-CAS-80-49-9.

Hyoscyamine (d, l)-CAS-101-31-5, hydrobromide salt-CAS-306-03-6 and sulfate salt-CAS-6835-16-1.

Scopolamine-CAS-51-34-3, hydrobromide salt-CAS-6533-68-2, methylbromide salt-CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chiropheniramine and its salts such as the maleate salt, and acrivastine.

Piperazines: hydroxyzine HCl, hydroxyzine pamoate, cyclizine HCl, cyclizine lactate, meclizine HCl, and cetirizine HCR.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a crystalline solvate of the invention.

Examples of preferred anti-histamines include methapyrilene and loratadine.

The invention thus provides, in a further aspect, a combination comprising a crystalline solvate of the present invention and a corticosteroid. As used herein, a crystalline solvate of the present invention means a monohydrochloride salt of compound 1 in solvate Form A, Form B, or a combination of Form A and Form B. In particular aspects, the invention provides combinations comprising a crystalline solvate of the present invention and fluticasone propionate; a crystalline solvate of the present invention and 6α,9α-difluoro-17α-[(2-furanylcarbonyl)oxy]-11β-hydroxy-16α-methyl-3-oxo-androsta-1,4-diene-17α-carbothioic acid S-fluoromethyl ester; and a crystalline solvate of the present invention and 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a crystalline solvate of the present invention and a PDE4 inhibitor.

The invention thus provides, in a further aspect, a combination comprising a crystalline solvate of the present invention and an anticholinergic agent.

The invention thus provides, in a further aspect, a combination comprising a crystalline solvate of the present invention and an antihistamine.

The invention thus provides, in a further aspect, a combination comprising a crystalline solvate of the present invention together with a PDE4 inhibitor and a corticosteroid.

The invention thus provides, in a further aspect, a combination comprising a crystalline solvate of the present invention together with an anticholinergic agent and a corticosteroid.

Accordingly, the pharmaceutical compositions of the invention can optionally comprise combinations of a crystalline solvate of the present invention with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art.

According to a further aspect, the invention provides a method of treating a disease or condition associated with $β_2$ adrenergic receptor activity in a mammal, comprising administering to the mammal a therapeutically effective amount of a combination of a crystalline solvate of the present invention with one or more other therapeutic agents.

Further, the present solvates, potentially can be formulated for other forms of administration, such as oral or parenteral administration. The solvates can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. Additional suitable pharmaceutical carriers for formulation of the crystalline solvates of the present invention can be found in *Remington: The Science and Practice of Pharmacy*, 20*th Edition*, Lippincott Williams & Wilkins, Philadelphia, Pa., 2000.

The following non-limiting examples illustrate representative pharmaceutical compositions of the invention, where active ingredient is defined as N-{2-[4-(3-phenyl-4-methoxyphenyl)aminophenyl]ethyl}-(R)-2-hydroxy-2-(8-hydroxy-2(1H)-quinolinon-5-yl)ethylamine, compound 1 in crystalline solvate Form A, crystalline solvate Form B, or a combination of Form A and Form B.

Formulation Example A

This example illustrates the preparation of a representative pharmaceutical composition for oral administration of the crystalline monoHCl salt of this invention:

| Ingredients | Quantity per tablet, (mg) |
| --- | --- |
| Active Ingredient | 1 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of the crystalline monoHCl salt of this invention:

| Ingredients | Quantity per tablet, (mg) |
| --- | --- |
| Active Ingredient | 1 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of the crystalline monoHCl salt of this invention.

An oral suspension is prepared having the following composition.

| Ingredients | |
|---|---|
| Active Ingredient | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Formulation Example D

This example illustrates the preparation of a representative pharmaceutical composition containing the crystalline monoHCl salt of this invention.

An injectable preparation buffered to a pH of 4 is prepared having the following composition:

| Ingredients | |
|---|---|
| Active Ingredient | 0.1 mg |
| Sodium Acetate Buffer Solution (0.4 M) | 2.0 mL |
| HCl (1N) | q.s. to pH 4 |
| Water (distilled, sterile) | q.s. to 20 mL |

Formulation Example E

This example illustrates the preparation of a representative pharmaceutical composition for injection using the crystalline monoHCl salt of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Formulation Example F

This example illustrates the preparation of a representative pharmaceutical composition for topical application of the crystalline monoHCl salt of this invention.

| Ingredients | grams |
|---|---|
| Active ingredient | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example G

This example illustrates the preparation of a representative pharmaceutical composition containing a compound of the invention.

An aqueous aerosol formulation for use in a nebulizer is prepared by dissolving 0.1 mg of the monoHCl salt of the invention in 1 mL of a 0.9% sodium chloride solution acidified with citric acid. The mixture is stirred and sonicated until the active salt is dissolved. The pH of the solution is adjusted to a value in the range of from 3 to 8 by the slow addition of NaOH.

Formulation Example H

This example illustrates the preparation of a dry powder formulation containing a the monoHCl salt of the invention for use in inhalation cartridges.

Inhalation cartridges are filled with a pharmaceutical composition having the following ingredients:

| Ingredients | mg/cartridge |
|---|---|
| Active ingredient | 0.2 |
| Lactose | 25 |

The active ingredient is micronized prior to blending with lactose. The contents of the cartridges are administered using a powder inhaler.

Formulation Example I

This example illustrates the preparation of a dry powder formulation containing the crystalline monoHCl salt of this invention for use in a dry powder inhalation device.

A pharmaceutical composition is prepared having a bulk formulation ratio of micronized active ingredient to lactose of 1:200. The composition is packed into a dry powder inhalation device capable of delivering between about 10 and about 100 μg of active drug ingredient per dose.

Formulation Example J

This example illustrates the preparation of a formulation containing the crystalline monoHCl salt of this invention for use in a metered dose inhaler.

A suspension containing 5% active ingredient, 0.5% lecithin, and 0.5% trehalose is prepared by dispersing 5 g of active compound as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example K

This example illustrates the preparation of a formulation containing the crystalline monoHCl salt of this invention for use in a metered dose inhaler.

A suspension containing 5% active ingredient and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

The following exemplify the preparation of N-{2-[4-(3-phenyl-4-methoxyphenyl)aminophenyl]ethyl}-(R)-2-hydroxy-2-(8-hydroxy-2(1H)-quinolinon-5-yl)ethylamine, compound 1; and preparation and characterization of crystalline Form A and crystalline Form B of the present invention.

EXAMPLE 1

Synthesis of 5-(2-bromo-1-oxy)ethyl-8-benzyloxy-2 (1H)-quinolinone (R)

a. Synthesis of 8-acetoxy-2(1H)-quinolinone (CC)

8-Hydroxyquinoline-N-oxide (160.0 g, 1.0 mol) and acetic anhydride (800 mL, 8.4 mol) were heated at 100° C. for 3 hours and then cooled in ice. The product was collected on a Buchner funnel, washed with acetic anhydride (2×100 mL) and dried under reduced pressure to give 8-acetoxy-2(1H)-quinolinone (CC) (144 g) as a tan solid.

b. Synthesis of 5-acetyl-8-hydroxy-2(1H)-quinolinone (DD)

A slurry of aluminum chloride (85.7 g, 640 mmol) in 1,2-dichloroethane (280 mL) was cooled in ice, and compound CC (56.8 g, 280 mmol) was added. The mixture was warmed to room temperature, and then heated at 85° C. After 30 minutes acetyl chloride (1.5 mL, 21 mmol) was added and the mixture was heated an additional 60 minutes. The reaction mixture was then cooled and added to 1N HCl (3 L) at 0° C. with stirring. After stirring for 2 hours, the solids were collected on a Buchner funnel, washed with water (3×250 mL) and dried under reduced pressure. The crude product isolated from several batches (135 g) was combined and triturated with dichloromethane (4 L) for 6 hours. The product was collected on a Buchner funnel and dried under reduced pressure to give 5-acetyl-8-hydroxy-2(1H)-quinolinone (DD) (121 g).

c. Synthesis of 5-acetyl-8-benzyloxy-2(1H)-quinolinone (EE)

To 5-acetyl-8-hydroxy-2-quinolone (37.7 g, 186 mmol) was added dimethylformamide (200 mL) and potassium carbonate (34.5 g, 250 mmol) followed by benzyl bromide (31.8 g, 186 mmol). The mixture was stirred at room temperature for 2.25 hour and then poured into saturated sodium chloride (3.5 L) at 0° C. and stirred well for 1 hour. The product was collected and dried on a Buchner funnel for 1 hour, and the resulting solids were dissolved in dichloromethane (2 L) and dried over sodium sulfate. The solution was filtered through a pad of Celite and washed with dichloromethane (5×200 mL). The combined filtrate was then concentrated to dryness and the resulting solids were triturated with ether (500 mL) for 2 hours. The product was collected on a Buchner funnel, washed with ether (2×250 mL) and dried under reduced pressure to give 5-acetyl-8-benzyloxy-2(1H)-quinolinone (EE) (44 g) as an off white powder.

d. Synthesis of 5-(2-bromo-1-oxy)ethyl-8-benzyloxy-2 (1H)-quinolinone (R)

5-Acetyl-8-benzyloxy-2(1H)-quinolinone (EE) (20.0 g, 68.2 mmol) was dissolved in dichloromethane (200 mL) and cooled to 0° C. Boron trifluoride diethyl etherate (10.4 mL, 82.0 mmol) was added via syringe and the mixture was warmed to room temperature to give a thick suspension. The suspension was heated at 45° C. (oil bath) and a solution of bromine (11.5 g, 72.0 mmol) in dichloromethane (100 mL) was added over 40 minutes. The mixture was kept at 45° C. for an additional 15 minutes and then cooled to room temperature. The mixture was concentrated under reduced pressure and then triturated with 10% aqueous sodium carbonate (200 mL) for 1 hour. The solids were collected on a Buchner funnel, washed with water (4×100 mL) and dried under reduced pressure. The product of two runs was combined for purification. The crude product (52 g) was triturated with 50% methanol in chloroform (500 mL) for 1 hour. The product was collected on a Buchner funnel and washed with 50% methanol in chloroform (2×50 mL) and methanol (2×50 mL). The solid was dried under reduced pressure to give 5-(2-bromo-1-oxy)ethyl-8-benzyloxy-2 (1H)-quinolinone (R) (34.1 g) as an off white powder.

EXAMPLE 2

Synthesis of N-{2-[4-(3-phenyl-4-methoxyphenyl) aminophenyl]ethyl}-(R)-2-hydroxy-2-(8-benzyloxy-2(1H)-quinolinon-5-yl)ethylamine (PP)

a. Synthesis of 5-(2-bromo-(R)-1-hydroxy)ethyl-8-benzyloxy-2(1H)-quinolinone (FF)

(R)-(+)-α,α-Diphenylprolinol (30.0 g, 117 mmol) and trimethylboroxine (11.1 mL, 78 mmol) were combined in toluene (300 mL) and stirred at room temperature for 30 minutes. The mixture was placed in a 150° C. oil bath and liquid was distilled off. Toluene was added in 20 mL aliquots, and distillation was continued for 4 hours. A total of 300 mL toluene was added. The mixture was finally cooled to room temperature. A 500 μL aliquot was evaporated to dryness, weighed (246 mg) to determine that the concentration of catalyst was 1.8 M.

5-(2-Bromo-1-oxy)ethyl-8-benzyloxy-2(1H)-quinolinone (R) (90.0 g, 243 mmol) was placed under nitrogen, tetrahydrofuran (900 mL) was added followed by the catalyst from above (1.8 M in toluene, 15 mL, 27 mmol). The suspension was cooled to −10+5° C. in an ice/isopropanol bath. Borane (1.0 M in THF, 294 mL, 294 mmol) was added over 4 hours. The reaction was stirred an additional 45 minutes at −10° C., then methanol (250 mL) was added slowly. The mixture was concentrated under vacuum. The residue was dissolved in boiling acetonitrile (1.3 L), filtered while hot and cooled to room temperature. The crystals were filtered, washed with acetonitrile and dried under vacuum to give 5-(2-bromo-(R)-1-hydroxy)ethyl-8-benzyloxy-2(1H)-quinolinone (FF) (72.5 g, 196 mmol, 81% yield, 95% ee, 95% pure by HPLC area ratio).

b. Synthesis of 5-(2-bromo-(R)-1-tert-butyldimethylsiloxy) ethyl-8-benzyloxy-2(1H)-quinolinone (HH)

Compound FF (70.2 g, 189 mmol) was treated with N,N-dimethylformamide (260 mL) and cooled in an ice bath under nitrogen. 2,6-Lutidine (40.3 g, 376 mmol) was added over 5 minutes followed slowly by tert-butyldimethylsilyl trifluoromethanesulfonate (99.8 g, 378 mmol), keeping the temperature below 20° C. The mixture was allowed to warm to room temperature for 45 minutes. Methanol (45 mL) was added to the mixture dropwise over 10 minutes and the mixture was partitioned between ethyl acetate/cyclohexane (1:1, 500 mL) and water/brine (1:1, 500 mL). The organics were washed twice more with water/brine (1:1, 500 mL each). The combined organics were evaporated under reduced pressure to give a light yellow oil. Two separate portions of cyclohexane (400 mL) were added to the oil and distillation continued until a thick white slurry was formed. Cyclohexane (300 mL) was added to the slurry and the resulting white crystals were filtered, washed with cyclohexane (300 mL) and dried under reduced pressure to give 5-(2-bromo-(R)-1-tert-butyldimethylsiloxy)ethyl-8-benzyloxy-2(1H)-quinolinone (HH) (75.4 g, 151 mmol, 80% yield, 98.6% ee).

c. Synthesis of N-[2-(4-bromophenyl)ethyl]-(R)-2-tert-butyldimethylsiloxy-2-(8-benzyloxy-2(1H)-quinolinon-5-yl)ethylamine (JJ)

Compound HH (136.5 g, 279 mmol), 4-bromophenethylamine (123 g, 615 mmol) and dimethyl sulfoxide (180 mL) were mixed at room temperature under nitrogen. Another 40 mL of dimethyl sulfoxide was added. The mixture was heated to 85° C. for 5 hours. The reaction was partitioned between ethyl acetate (1 L) and 10% aqueous acetic acid (500 mL). The organics were washed with 10% aqueous acetic acid (3×500 mL), then with 1N sodium hydroxide (3×500 mL). The last wash was filtered through Celite (100 g). The organic layer was concentrated to 300 mL and cyclohexane (2×500 mL) was added and the solution concentrated to 300 mL. Sufficient cyclohexane was added to form 1.8 L final volume which was filtered through Celite (50 g). A solution of HCl in isopropanol, prepared by slowly adding concentrated HCl (23.5 mL) to isopropanol (180 mL) at 10° C. (internal), was added to the crude product and the reaction mixture was stirred for 5 hours, washed with cyclohexane (2×500 mL) and dried under reduced pressure for 24 hours to give N-[2-(4-bromophenyl)ethyl]-(R)-2-tert-butyldimethylsiloxy-2-(8-benzyloxy-2(1H)-quinolinon-5-yl)ethylamine (JJ) hydrochloride (145 g, 80 mol %, 106 wt %, HPLC purity 97.9%).

d. Synthesis of N-{2-[4-(3-phenyl-4-methoxyphenyl)aminophenyl]ethyl}-(R)-2-tert-butyldimethylsilyl -2-(8-benzyloxy-2(1H)-quinolinon-5-yl)ethylamine (NN)

To compound JJ hydrochloride (73.7 g, 114 mmol) and 4-methoxy-3-phenylaniline hydrochloride (32.4 g, 137 mmol), toluene (380 mL) was added with mild agitation for 5 minutes, followed by sodium tert-butoxide (49.3 g, 513 mmol) in portions over 1 minute, and finally 2,2'-bis(diphenylphosphino)-1,1'-binaphthyl (10.65 g, 17 mmol) and tris (dibenzylideneacetone)dipalladium(0) (5.22 g, 5.7 mmol). The resulting mixture was stirred and heated to 85–89° C. (internal) for 2.5 hours. The solution was cooled to room temperature, water (400 mL) was added and the mixture was stirred for 5 minutes, filtered through Celite (80 g), and partitioned with toluene (100 mL). The organic layer was collected and concentrated under reduced pressure in a 40° C. bath to give N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN) as a dark viscous oil.

e. Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Compound NN from the previous step was dissolved in 280 ml of THF. Triethylamine trihydrofluoride (27.6 g, 171 mmol) was added to the solution, an additional 20 mL of THF was used to rinse down residual reagent, and the reaction was stirred at 25° C. under nitrogen for 16 hours. The reaction mixture was concentrated under reduced pressure in a 25° C. bath to give a dark viscous oil to which dichloromethane (400 mL) was added, followed by 1N aqueous NaOH (200 mL). The reaction mixture was stirred for 5 hours. The top layer was discarded and the organic layer was concentrated to a viscous oil.

The oil was dissolved in dichloromethane to give a total volume of 630 mL. A 60 mL aliquot was taken and concentrated to 30 mL. Toluene (60 mL) was added, followed by a mixture of concentrated hydrochloric acid (2.7 mL) and methanol (4.5 mL) to give a thick paste covered in a free-flowing liquid. The liquid was carefully removed and the paste washed with toluene (50 mL). The gum was partitioned between dichloromethane (40 mL) and 1N aqueous sodium hydroxide (40 mL) and the organic solvents were removed under reduced pressure. The residue was purified chromatographically over silica using a gradient of 0–10% methanol in dichloromethane to give N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (98.6% pure by HPLC area ratio).

EXAMPLE 3

Purification of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

To free the material produced by the process of Examples 1 and 2 of palladium, intermediate PP (0.5 g, 0.82 mmol, Pd level ~850 ppm by ICP) was dissolved in 1:1 dichloromethane:methanol (5 mL) and 4M hydrochloric acid in dioxane (0.445 mL, 1.78 mmol) was added. The resulting dark brown solution was diluted further with dichloromethane (7.5 mL) and 3-(1-thioureido)propyl functionalized silica gel (0.05 g) was added (Sigma-Aldrich, St. Louis, Mo.). The suspension was stirred at room temperature for 20 h followed by filtration through filter paper. The remaining yellow silica was washed with a mixture of 5 mL of methanol and 30 mL of dichloromethane. Combined organic solutions were washed with saturated aqueous sodium bicarbonate (50 mL) and brine (50 mL). The organic solution was treated with anhydrous sodium sulfate for 30 minutes, filtered and evaporated under reduced pressure to give N-{2-[4-(3-phenyl-4methoxyphenyl)aminophenyl]ethyl}-(R)-2-hydroxy-2-(8-benzyloxy-2(1H)-quinolinon-5-yl)ethylamine (PP) (~90% yield, Pd level by ICP 30 ppm, purity 97.4% by HPLC area ratio).

EXAMPLE 4

Synthesis of N-{2-[4-(3-phenyl-4-methoxyphenyl)aminophenyl]ethyl}-(R)-2-hydroxy-2-(8-hydroxy-2 (1H)-quinolinon-5-yl)ethylamine (1) hydrochloride To compound PP from the previous step (2.1 g, 3.43 mmol) was added under nitrogen 10% palladium on carbon (420 mg) followed by ethylene glycol (16 mL) and concentrated hydrochloric acid (0.57 mL, 6.9 mmol). The suspension was stirred vigorously under 1 atmosphere of hydrogen for 5 h. The solids were filtered off and washed with ethylene glycol (5 mL). The filtrate was warmed to 50° C. and water (21 mL) was added over 5 minutes under stirring. A brown gum formed which broke up to an off-white solid under continued stirring at 50° C. for 40 min. The solid was filtered off, with water (2×20 mL) and air dried to afford an amorphous hydrochloride salt of compound 1 (2.5 g containing 44.3% water, 74% yield)

To improve the purity of the title compound, (2.5 g, 4.8 mmol) was dissolved in methanol (25 mL) at 40° C. The dark blue solution was cooled to room temperature, decolorizing charcoal (Darco-KB, 2.5 g) was added and the suspension stirred at room temperature overnight. Solids were filtered off over Celite (2.0 g), filter cake was washed with methanol (2×10 mL) and solvent was evaporated under reduced pressure to leave and amorphous hydrochloride salt of N-{2-[4-(3-phenyl-4-methoxyphenyl)aminophenyl]ethyl}-(R)-2-hydroxy-2-(8-hydroxy-2(1H)-quinolinon-5-yl)ethylamine (1) as a light gray solid (1.5 g).

EXAMPLE 5

Crystallization of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water/isopropanol solvate (Form A)

The product of Example 4 (1.0 g, 1.68 mmol) was suspended in 50% isopropanol/water (10 mL) and heated to 50° C. under stirring. The amorphous material does not completely dissolve before off-white crystals start to appear. After 90 min the heating bath was turned off and the suspension allowed to cool to room temperature over 16 h. The crystalline solid was collected by filtration and washed with 50% isopropanol/water (10 mL) and isopropanol (3 mL). The filter cake was air-dried for one hour then dried under vacuum until the loss on drying was less than 7%. The loss on drying was determined by drying a small aliquot to completion at high temperature to determine the fraction of a solid sample due to volatile solvents. Crystallization yielded 803 mg of material that was 97.8% pure by HPLC area ratio. The material contained 3.2% water (analysis by the Karl Fischer method) and 3.6% isopropanol (analysis by $^1$H NMR).

EXAMPLE 6

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (1) hydrochloride To a solution of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) prepared by the process of Examples 1 and 2 (4.0 g, 6.5 mmol) in tetrahydrofuran (100 mL) and water (16 mL) was added 10% palladium on carbon (800 mg). The reaction was stirred vigorously under one atmosphere of hydrogen for 6.5 h. The solids were filtered off and washed with tetrahydrofuran (4×25 mL) and then 50% methanol/tetrahydrofuran (2×25 mL). The combined filtrates were evaporated to dryness and the crude product was purified by reverse-phase HPLC. Fractions containing pure product were combined and lyophilized. The product from several runs was combined to give 4.68 g which was dissolved in acetonitrile (200 mL) and water (200 mL). 1.0 N HCl (18.7 mL) was added, and the solution was lyophilized. The residue was again dissolved in acetonitrile (125 mL) and water (125 mL). 1.0 N HCl was added and the solution was lyophilized to give an amorphous hydrochloride salt of compound 1 as an off white powder. $^1$H NMR (300 MHz, DMSO-d6) δ 10.55 (br s, 1H), 9.40 (br s, 1H), 8.80, (br s, 1H), 8.26 (d, 1H), 7.60, (br s, 2H) 7.25–7.45 (m, 5H), 6.92–7.16 (m 10H), 6.55 (d, 1H), 5.45 (d, 1H), 3.69 (s, 3H) 2.80–3.15 (m, 6H); m/z: [M+H$^+$] calcd for $C_{32}H_{31}N_3O_4$ 522.24; found 522.4.

EXAMPLE 7

Crystallization of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water/isopropanol solvate (Form A)

The product of Example 6 was taken up in 10 mL/g of 50% isopropanol/water and warmed to 50° C. under stirring. After 2 h the bath was removed and the suspension allowed to cool to room temperature over several hours. An additional 10 mL/g of 50% isopropanol/water was added and the heating cycle repeated. After 2 h the suspension was allowed to cool slowly overnight by turning off the heating bath. The solid product was isolated by filtration and dried as described in Example 5.

EXAMPLE 8

Characterization of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water/isopropanol solvate (Form A)

The x-ray powder diffraction pattern and differential scanning calorimetry and thermogravimetric analysis traces of a lot of Form A material produced by the process of Example 7 are shown in FIGS. 1 and 2 respectively. The material was further characterized as follows: $^1$H NMR (300 MHz, DMSO-d6) δ 10.55 (br s, 1H), 9.40 (br s, 1H), 8.80, (br s, 1H), 8.26 (d, 1H), 7.60, (br s, 2H) 7.25–7.45 (m, 5H), 6.92–7.16 (m 10H), 6.55 (d, 1H), 5.45 (d, 1H), 3.69 (s, 3H) 2.80–3.15 (m, 6H); m/z: [M+H$^+$] cald for $C_{32}H_{31}N_3O_4$ 522.24; found 522.4. IR: 626, 638, 643, 698, 829, 1048, 1233, 1261, 1301, 1399, 1490, 1508, 1598, 1640, and in the range 3360–3480 cm$^{-1}$. Water content: 3.44%. Residual solvent by headspace GC: 3.42% isopropanol. Elemental analysis (wt %) calculated for $C_{32}H_{32}N_3O_4Cl$ incl. 3.4% (1.15 mol) $H_2O$ and 3.4% (0.33 mol) isopropanol: C, 66.14; H, 6.22; N, 7.01; Cl, 5.92. Found: C, 66.57; H, 6.16; N, 6.99; Cl, 6.16.

EXAMPLE 9

Preparation of N-{2-[4-(3-phenyl-4-methoxyphenyl)aminophenyl]ethyl}-(R)-2-hydroxy-2-(8-hydroxy-2(1H)-quinolinon-5-yl)ethylamine (1)

The free base form of compound 1 was prepared from the protected intermediate PP. To a solution of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) prepared by the process of Examples 1 and 2 (43.0 g, 70 mmol) in 50% dichloromethane/methanol (200 mL) was added 20% palladium on carbon (8.6 g). The reaction was stirred vigorously under one atmosphere of hydrogen for 18 h. The solids were filtered off over Celite and washed with 50% dichloromethane/methanol (4×25 mL). The combined filtrates were evaporated to dryness to give compound 1 (38 g, purity 92% by HPLC ratio) as a gray solid.

EXAMPLE 10

Crystallization of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water/isopropanol solvate (Form A)

Compound 1 (0.5 g) was suspended in a mixture of 2.5 mL isopropanol, 0.5 mL water and 2.0 mL 1N HCl (2.0 eq) (amounting to a mix of 5 mL 50% isopropanol/aqueous medium at a concentration of 10 mL/g). The suspension was warmed to 50° C. under stirring. After ~70% of starting material had dissolved, off-white crystals started to precipitate. Stirring and heating was continued for 2 h while the remaining starting material dissolved and more crystalline material formed. The heating bath was removed, the suspension allowed to cool to room temperature for 2 h and the solids were removed by filtration and dried (465 mg). A small sample was retained for analysis and the remaining material was recrystallized as follows.

The remaining solid material was suspended in 4.5 mL of 50% isopropanol/water. The suspension was stirred and warmed to 50° C. for 2 h. After allowing to cool to room temperature overnight the suspension was filtered as described above. The filter cake was washed with 50% isopropanol/water (2 mL) and isopropanol (2 mL). After suction-drying for an hour the filter cake was dried under vacuum to give Form A as an off white solid (332 mg). XRPD analysis showed a crystalline solid.

EXAMPLE 11

Preparation of N-{2-[4-(3-phenyl-4-methoxyphenyl) aminophenyl]ethyl}-(R)-2-hydroxy-2-(8-hydroxy-2 (1H)-quinolinon-5-yl)ethylamine (1) monohydrochloride water hydrate (Form B)

The crystalline product of Example 5 (Form A) (8.5 g, 15.2 mmol, containing 3.8% isopropanol by $^1$H NMR was transferred to a 500 mL round bottomed flask equipped with a overhead stirrer. Deionized water (250 mL) was added and the suspension was stirred at room temperature under medium stirring speed. Samples for analysis were filtered, washed with water and dried for 30 min before taking an NMR spectrum. After 18 h of slurrying, the material contained 1.1% isopropanol. After 24 h of stirring the suspension was filtered through a medium speed filter paper and the moist filter cake re-suspended in 250 mL of water. After another 18 h of stirring (42 h of total stirring time) the IPA level had dropped to 0.4% and after a total of 48 h $^1$H NMR showed an IPA level of 0.3%. The slurry was filtered through medium speed filter paper and air-dried for 30 min. The still moist filter cake was transferred to a crystallizing dish, spread thin and dried in a vacuum oven at room temp. under house vacuum. After 24 h of drying the water level was determined to be 6.5% (analysis by Karl Fischer method), and after 29 h the water level was 4.3%. The process yielded 7.6 g of N-{2-[4-(3-phenyl-4-methoxyphenyl)aminophenyl] ethyl}-(R)-2-hydroxy-2-(8-hydroxy-2(1H)-quinolinon-5-yl) ethylamine (1) monohydrochloride water hydrate (Form B) that was crystalline by XRPD.

EXAMPLE 12

Characterization of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water hydrate (Form B)

The x-ray powder diffraction pattern and differential scanning calorimetry and thermogravimetric analysis traces of a lot of Form B material produced by the process of Example 11 are shown in FIGS. 3 and 4 respectively. The material was further characterized as follows: $^1$H NMR (300 MHz, DMSO-d6) δ 10.52 (br s, 1H), 8.23 (d, 1H), 7.95, (s, 2H) 7.46–7.27 (m, 5H), 6.92–7.16 (m 10H), 6.55 (d, 1H), 6.17 (bs, 1H), 5.43 (d, 1H), 3.70 (s, 3H) 2.90–3.15 (m, 6H); m/z: [M+H$^+$] calcd for $C_{32}H_{31}N_3O_4$ 522.24; found 522.3. IR: 653, 698, 829, 1232, 1262, 1383, 1445, 1488, 1508, 1548, 1598, 1640, 2831, 3033, 3388. Water content 5.4%. Residual solvent by headspace GC: 0.2% isopropanol.

EXAMPLE 13

Solid state stability testing of N-{2-[4-(3-phenyl-4-methoxyphenyl)aminophenyl]ethyl}-(R)-2-hydroxy-2-(8-hydroxy-2(1H)-quinolinon-5-yl)ethylamine (1) monohydrochloride water/isopropanol solvate (Form A)

Samples (20 and 80 mg each) of the Form A material produced by the process of Example 7 were stored at 25° C. and 60% relative humidity and at 40° C. and 75% relative humidity in open containers and in closed containers. After four weeks, for the material stored at 25° C. and 60% relative humidity in closed containers, analysis by DSC and TGA showed no detectable differences, and analysis by HPLC showed no detectable chemical degradation. The material stored in open containers showed loss of isopropanol over the course of four weeks.

Analytical Methods

X-ray powder diffraction patterns were obtained with a Shimadzu 6000 diffractometer using Cu Kα (40.0 kV, 35.0 mA) radiation. The analysis was performed with the goniometer running in continuous-scan mode of 2°/min with a step size of 0.020 over a range of 4 to 45°. Samples were prepared on glass specimen holders as a thin layer of powdered material. The instruments was calibrated to a silicon metal standard.

Differential scanning calorimetry traces were obtained with a TA instruments model DSCQ10. Samples were placed in sealed aluminum pans for analysis with an empty pan serving as the reference. Samples were equilibrated at 30° C. and heated at 5° C. per minute to a temperature of 300° C. The instrument was calibrated with an indium standard.

Thermogravimetric analysis was conducted using a TA instruments model Q50. Samples were weighed in aluminum pans and heated from 30° C. to 300° C. at a rate of 5° C./min.

The IR spectrum was determined over the wave number (v) range 4000 to 675 cm$^{-1}$ using an Avatar 360 FT-IR spectrometer equipped with a Nicolet omnis sample attenuated total reflection (ATR) sample holder.

$^1$H NMR spectra were acquired on a 300 MHz Varian Gemini 2000 spectrometer at ambient temperature. Samples were dissolved in DMSO-d6 and chemical shifts were reported on a TMS scale using residual DMSO protons (2.49 ppm) as reference. $^{13}$C NMR spectra were acquired on JEOL Eclipse$^+$400 MHz spectrometer.

HPLC analysis was performed using reverse phase conditions and a gradient of 2% to 90% acetonitrile over 6 minutes. Solvents contain 0.1% trifluoroacetic acid. Column: Zorbax 2.1×50 mm, flow rate 0.5 mL/min, observed wavelength 214 nm.

Mass spectrometric identification was performed by an electrospray ionization method (ESMS) with a Perkin Elmer instrument (PE SCIEX API 150 EX).

Elemental percentages of carbon, hydrogen, and nitrogen were determined by combustion analysis. Percentage of chlorine was determined by titration.

Water content was determined by coulometric Karl Fischer titration using a Brinkman Metrohm Karl Fischer Model 831 coulometer.

Residual solvents were determined by gas chromatography (GC) with headspace sampling and Flame Ionization Detection (FID) using an Agilent 6890 GC, Agilent 7694 headspace sampler and a 30 cm×0.53 mm×3 μm J&W DB-624 capillary column.

Palladium levels were determined by the technique of Inductively Coupled Plasma (ICP) spectroscopy, based on measurement of atomic line emission spectra produced by a radio frequency inductively coupled plasma, using a Perkin Elmer Optima 3100 DV instrument.

Chiral purity was determined by chiral HPLC: Samples were analyzed using isocratic conditions with a mobile phase of 100% methanol buffered with 0.5% each acetic acid and triethylamine. Column: Astec Chirobiotic V 4.6×250 mm, flowrate 0.4 mL/min, observed wavelength: 220 nm.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. Crystalline N-{2-[4-(3-phenyl-4-methoxyphenyl)aminophenyl]ethyl}-(R)-2-hydroxy-2-(8-hydroxy-2(1H)-quinolinon-5-yl)ethylamine monohydrochloride in solvate form wherein the solvate form is a crystalline water and isopropanol solvate or crystalline water hydrate solvate.

2. The compound of claim 1 wherein the solvate form is a water and isopropanol solvate.

3. The compound of claim 2 which is characterized by an x-ray powder diffraction pattern having two or more diffraction peaks at 2θ values selected from the group consisting of 13.12±0.2, 13.66±0.2, 15.56±0.2, 15.68±0.2, 17.39±0.2, 18.39±0.2, 19.32±0.2, 19.61±0.2, 20.42±0.2, 21.38±0.2, 21.72±0.2, 22.95±0.2, 23.50±0.2, 23.99±0.2, and 24.60±0.2.

4. The compound of claim 2 which is characterized by an x-ray powder diffraction pattern having two or more diffraction peaks at 2θ values selected from the group consisting of 19.61±0.2, 20.42±0.2, 21.38±0.2, 21.72±0.2, and 24.60±0.2.

5. The compound of claim 2 which is characterized by an x-ray powder diffraction pattern in which the peak positions are substantially in accordance with the peak positions of the pattern shown in FIG. 1.

6. The compound of claim 2 having an infrared absorption spectrum with significant absorption bands at 626±1, 638±1, 643±1, 656±1, 698±1, 829±1, 1048±1, 1233±1, 1301±1, 1399±1, 1490±1, 1508±1, 1598±1, 1640±1, and in the range 3360–3480 cm$^{-1}$.

7. The compound of claim 2 which is characterized by a differential scanning calorimetry trace substantially in accordance with the trace shown in FIG. 2.

8. The compound of claim 2 wherein the compound comprises between about 2% and about 4% by weight water and between about 2% and about 4% by weight isopropanol.

9. The compound of claim 1 wherein the solvate form is a water hydrate.

10. The compound of claim 9 which is characterized by an x-ray powder diffraction pattern having two or more diffraction peaks at 2θ values selected from the group consisting of 13.26±0.2, 13.72±0.2, 15.66±0.2, 15.87±0.2, 17.43±0.2, 18.54±0.2, 19.44±0.2, 19.70±0.2, 20.54±0.2, 21.54±0.2, 21.82±0.2, 23.08±0.2, 24.12±0.2, and 24.69±0.2.

11. The compound of claim 9 which is characterized by an x-ray powder diffraction pattern having two or more diffraction peaks at 2θ values selected from the group consisting of 20.54±0.2, 21.82±0.2, 23.08±0.2, 24.12±0.2, and 24.69±0.2.

12. The compound of claim 9 which is characterized by an x-ray powder diffraction pattern in which the peak positions are substantially in accordance with the peak positions of the pattern shown in FIG. 3.

13. The compound of claim 9 having an infrared absorption spectrum with significant absorption bands at 653±1, 698±1, 829±1, 1232±1, 1262±1, 1383±1, 1445±1, 1488±1, 1508±1, 1548±1, 1598±1, 1640±1, 2831±1, 3033±1, and 3388±1 cm$^{-1}$.

14. The compound of claim 9 which is characterized by a differential scanning calorimetry trace substantially in accordance with the trace shown in FIG. 4.

15. The compound of claim 9 wherein the compound comprises between about 2% and about 7% by weight water.

16. A pharmaceutical composition comprising a therapeutically effective amount of the compound of claim 1 and a pharmaceutically acceptable carrier.

17. The pharmaceutical composition of claim 16, wherein the composition further comprises a therapeutically effective amount of one or more other therapeutic agents.

18. The pharmaceutical composition of claim 16, wherein the composition is formulated for administration by inhalation.

19. A combination comprising the compound of claim 1 and one or more other therapeutic agents.

20. The combination of claim 19 wherein the other therapeutic agent is a corticosteroid, an antichlolinergic agent, or a PDE4 inhibitor.

21. A combination comprising the compound of claim 1 and 6α,9α-difluoro-11β-hydroxy-16α-methyl-17α-[(4-methyl-1,3-thiazole-5-carbonyl) oxy]-3-oxo-androsta-1,4-diene-17β-carbothioic acid S-fluoromethyl ester or 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

22. A method of treating a disease or condition associated with β$_2$ adrenergic receptor activity in a mammal, the method comprising administering to the mammal, a therapeutically effective amount of a compound of claim 1.

23. The method of claim 22 wherein the disease or condition is a pulmonary disease.

24. The method of claim 23 wherein the pulmonary disease is asthma or chronic obstructive pulmonary disease.

25. The method of claim 22 wherein the method further comprises administering a therapeutically effective amount of one or more other therapeutic agents.

26. The method of claim 25 wherein the other therapeutic agent is a corticosteroid, an antichlolinergic agent, or a PDE4 inhibitor.

27. A process for preparing the compound of claim 2, the process comprising the steps of:
  (a) suspending N-{2-[4-(3-phenyl-4-methoxyphenyl)aminophenyl]ethyl}-(R)-2-hydroxy-2-(8-hydroxy-2(1H)-quinolinon-5-yl)ethylamine hydrochloride in a polar solvent comprising isopropanol and water;
  (b) heating the suspension to between about 40° C. and about 60° C.; and
  (c) cooling the suspension to room temperature, resulting in the formation of the compound of claim 2.

28. A process for preparing the compound of claim 2, the process comprising the steps of:
  (a) suspending N-{2-[4-(3-phenyl-4-methoxyphenyl)aminophenyl]ethyl}-(R)-2-hydroxy-2-(8-hydroxy-2(1H)-quinolinon-5-yl)ethylamine in a polar solvent comprising isopropanol, water, and a molar excess of hydrochloric acid;
  (b) heating the suspension to between about 40° C. and about 60° C.; and
  (c) cooling the suspension to room temperature, resulting in the formation of the compound of claim 2.

29. A process for preparing the compound of claim 9, the process comprising the steps of:
  (a) forming a first water slurry of crystalline N-{2-[4-(3-phenyl-4-methoxyphenyl)aminophenyl]ethyl}-(R)-2-hydroxy-2-(8-hydroxy-2(1H)-quinolinon-5-yl)ethylamine hydrochloride water and isopropanol solvate;
  (b) isolating a solid material from the first water slurry
  (c) forming a second water slurry from the isolated solid material from which the compound of claim 9 is obtained.

30. A method of reducing the amount of palladium in a composition comprising the diarylamine compound N-{2-[4-(3-phenyl-4-methoxyphenyl)aminophenyl]ethyl}-(R)-2-hydroxy-2-(8-benzyloxy-2(1H)-quinolinon-5-yl)ethylamine and palladium, the method comprising the steps of:
  (a) contacting a solution comprising the diarylamine compound wherein each nitrogen atom in the diarylamine compound has been protonated with an acid, palladium, and a solvent, with a functionalized solid support comprising (1-thioureido)alkyl or (mercapto)alkyl groups; and
  (b) separating the resulting solution from the solid support to provide a composition having a reduced amount of palladium;
wherein the solvent is compatible with the functionalized solid support.

31. The method of claim 30 wherein the acid is hydrochloric acid, the solvent comprises dichloromethane and methanol and the functionalized solid support is a functionalized silica gel comprising 3-(1-thioureido)propyl or 3-(mercapto)propyl groups.

* * * * *